United States Patent
Makdissi

(10) Patent No.: US 8,849,383 B2
(45) Date of Patent: *Sep. 30, 2014

(54) NON-LINEAR FILTERING FOR THE RECONSTRUCTION OF A SURFACE ELECTROCARDIOGRAM FROM AN ENDOCARDIAL ELECTROGRAM

(71) Applicant: Sorin CRM S.A.S., Clamart (FR)

(72) Inventor: Alaa Makdissi, Paris (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,890

(22) Filed: Sep. 9, 2013

(65) Prior Publication Data

US 2014/0073894 A1     Mar. 13, 2014

Related U.S. Application Data

(63) Continuation of application No. 12/731,009, filed on Mar. 24, 2010, now Pat. No. 8,532,753.

(30) Foreign Application Priority Data

Mar. 25, 2009   (FR) ...................................... 09 01399

(51) Int. Cl.
| | |
|---|---|
| A61B 5/04 | (2006.01) |
| A61B 5/02 | (2006.01) |
| A61B 5/042 | (2006.01) |
| A61N 1/08 | (2006.01) |
| A61N 1/05 | (2006.01) |
| A61B 5/00 | (2006.01) |
| A61B 5/0432 | (2006.01) |
| A61N 1/37 | (2006.01) |
| A61N 1/39 | (2006.01) |
| A61B 5/0402 | (2006.01) |

(52) U.S. Cl.
CPC ........... *A61B 5/04017* (2013.01); *A61B 5/0422* (2013.01); *A61N 1/08* (2013.01); *A61N 1/0563* (2013.01); *A61B 5/725* (2013.01); *A61B 5/0432* (2013.01); *A61N 1/3702* (2013.01); *A61B 5/7267* (2013.01); *A61N 1/3925* (2013.01); *A61B 5/042* (2013.01); *A61B 5/04028* (2013.01); *A61B 5/04021* (2013.01)
USPC ............ 600/509; 600/300; 600/511; 600/512

(58) Field of Classification Search
USPC ................................ 600/300, 509, 511–512
See application file for complete search history.

(56) References Cited

U.S. PATENT DOCUMENTS

| 5,740,811 A | 4/1998 | Hedberg et al. |
| 5,938,594 A | 8/1999 | Poon et al. |

(Continued)

FOREIGN PATENT DOCUMENTS

| EP | 1 902 750 | 3/2008 |
| WO | WO-2008/008692 | 1/2008 |

OTHER PUBLICATIONS

Preliminary Search Report for French Patent Application No. FR 0901399, dated Oct. 6, 2009, 2 pages.

*Primary Examiner* — Nicole F Lavert
(74) *Attorney, Agent, or Firm* — Foley & Lardner LLP

(57) ABSTRACT

An active medical device using non-linear filtering for the reconstruction of a surface electrocardiogram (ECG) from an endocardial electrogram (EGM) is disclosed. The device for the reconstruction of the surface ECG comprises: a plurality of inputs, receiving a corresponding plurality of EGM signals from endocardial or epicardial electrogram ($x_1[n]$, $x_2[n]$), each collected on a respective EGM derivation of a plurality of EGM derivations, and at least one output delivering a reconstructed surface ECG electrocardiogram signal ($y[n]$), related to an ECG derivation, and a non-linear digital filter (12', 12', 14) with a transfer function that determines the reconstructed ECG signal based on said plurality of input EGM signals. The non-linear digital filter includes a Volterra filter type (12, 12', 12") whose transfer function includes a linear term (h1) and at least one quadratic (h2) and/or cubic (h3) term(s).

16 Claims, 2 Drawing Sheets

(56) References Cited

U.S. PATENT DOCUMENTS

| | | | |
|---|---|---|---|
| 6,980,850 | B1 | 12/2005 | Kroll et al. |
| 7,383,080 | B1 | 6/2008 | Kil et al. |
| 7,979,112 | B2 | 7/2011 | Molin et al. |
| 8,050,749 | B2 | 11/2011 | Dal Molin et al. |
| 8,060,198 | B2 | 11/2011 | Lian et al. |

NON-LINEAR FILTERING FOR THE RECONSTRUCTION OF A SURFACE ELECTROCARDIOGRAM FROM AN ENDOCARDIAL ELECTROGRAM

CROSS-REFERENCE TO RELATED APPLICATIONS

This present application is a continuation of U.S. application Ser. No. 12/731,009, now issued as U.S. Pat. No. 8,532,753, filed Mar. 24, 2010, which claims the benefit of French Patent Application No. 0901399, filed Mar. 25, 2009. Both U.S. Pat. No. 8,532,753 and French Patent Application No. 0901399 are incorporated by reference herein in their entireties.

FIELD OF THE INVENTION

The present invention relates to "implantable medical devices" such as those defined by the Jun. 20, 1990 Directive 90/385/EEC of the Council of European Communities, specifically to implantable devices that continuously monitor heart rhythm and deliver to the heart, if necessary, electrical stimulation pulses for cardiac resynchronization and/or defibrillation The invention more particularly relates to processing the signals representative of cardiac depolarization potentials of the myocardium, such signals being collected through epicardial or endocardial electrodes for pacing, sensing or defibrillation of the right and left atria or ventricles, of these implantable devices.

Even more particularly, the present invention is directed to a method, whether or not implemented in that implanted device, for the reconstruction of a surface electrocardiogram (ECG) from an endocardial or epicardial electrogram (EGM).

BACKGROUND OF THE INVENTION

It is known that EGM signals are collected by use of electrodes placed on endocardial or epicardial leads of a device implanted in a patient. These signals, directly related to electrical activities of cardiac cells of the patient, provide much useful information for the purpose of assessing the patient's condition. Hence, after amplifying, conditioning, digitizing and filtering, EGM signals are mainly utilized to control the implanted device and diagnose rhythm disorders requiring, for example, automatic triggering of an antitachycardia, antibradycardia, or interventricular resynchronization therapy.

However, when it comes to analyzing subjectively the cardiac rhythm, e.g., to perform a diagnosis or to readjust the control/operating parameters of an implanted device, practitioners prefer, in practice, to interpret the information given by a surface electrocardiogram (ECG). A surface ECG allows one to visualize in a direct manner, certain determining factors (e.g., QRS width) and thereby assess the evolution of a cardiac failure.

ECG signals are usually recorded over a long period of time through ambulatory practice by Holter recorders. The recorded ECG signals are then further processed and analyzed in order to evaluate the clinical condition of the patient and eventually diagnose whether a cardiac rhythm disorder is present.

The ECG and EGM signals actually have the same signal source, i.e., electrical activities of the myocardium, however they visually appear in much different manners: the EGM collected by the implantable device provides local information on electrical activities of a group of heart cells, whereas the ECG appears in the form of more global information, in particular influenced by the propagation of electrical signals between the myocardium and body surface with certain morphologic and pathologic specificities. Thus, the display of EGM signals is not very useful to a practitioner who interprets ECG signals.

When a patient implanted with a medical device comes to his/her practitioner for a routine visit, two distinct devices are used: an ECG recorder and an external implant programmer. In order to collect ECG signals, the practitioner places electrodes in particular locations of the patient's torso. The ECG signals are collected between predefined pairs of electrodes to define typically twelve derivations of the collected ECG signals. The external programmer is used to control certain operating parameters of the implanted device (e.g., the battery life), download data from the memory of the implantable device, modify the parameters thereof, or upload an updated version of the device operating software, etc.

The visit with the practitioner therefore usually requires two different devices, as well as specific manipulations for placing the surface electrodes and collecting the ECG signals.

Moreover, the use of these two devices requires the patient to come to a specifically equipped center, usually having the consequence that routine visits are spaced farther apart, resulting in a less rigorous follow-up of the patient.

Furthermore, the ECG recording has various drawbacks, notably:

the preparation of the patient which requires a certain time, correlated with a globally increased follow-up cost;

the local irritation of the skin created by fixing of the electrodes in some patients;

the position of the electrodes varies from one visit to another, inducing variations in the reconstructed ECG;

the ECG recording is affected by several parameters that are difficult to control, such as breathing, movements of the patient, as well as the interferences emitted by various external electrical sources.

In order to overcome such drawbacks, some algorithms have been developed for reconstruction of the ECG based upon EGM signals that are directly provided by the implanted device. Indeed, reconstruction of the ECG based upon EGM signals would:

avoid, during routine visits, having to place surface electrodes and resort to an ECG recorder;

render a patient's visit simpler and quicker, eventually allow performing a routine visit at the patient's home, and subsequently shorten the intervals between successive visits, and improve the patient's follow-up; and allow a remote transmission of the EGM data recorded by the implanted device, without the intervention of a practitioner or a medical aid.

Various algorithms for ECG reconstruction based upon EGM signals have been previously proposed.

U.S. Pat. No. 5,740,811 (Hedberg, et al.) proposes to synthesize an ECG signal by combining a plurality of EGM signals by means of a neural network, fuzzy logic, and/or summer circuit, after a learning process by a "feedforward" type algorithm. This technique does not take into account the propagation time delay between the EGM signals and the surface ECG signals leading to a precision loss in the reconstructed ECG signal. Another drawback of such technique is that it does not take into account the varying position of the endocardial leads between the moment of the learning process and that of the use of the device; a change in the heart electrical axis may bias the synthesized ECG signal, generating a misleading ECG signal. A cardiac disorder that is masked by the biased synthesis may not be accurately diagnosed.

U.S. Pat. No. 6,980,850 (Kroll et al.) proposes to overcome this difficulty, by proposing a method of surface ECG reconstruction implementing a matrix transform allowing to render each of the ECG derivations individually. Such transform also allows to take into account several parameters, such as patient's respiratory activity or posture that influence tracking the position of the endocardial leads through space. The proposed reconstruction consists of transforming, through a predetermined transfer matrix, an input vector representative of a plurality of EGM signals into a resulting vector representative of the different ECG derivations. The transfer matrix is learned through averaging several instantaneous matrices based upon ECG and EGM vectors recorded simultaneously over the same period of time.

Although this last technique brings an improvement to that proposed in U.S. Pat. No. 5,740,811, it nevertheless presents certain drawbacks. First, it makes an assumption that there exists a linear relationship between ECG and EGM vectors: such an approximation, though relatively accurate with patients presenting a regular rhythm, leads in some cases to large errors of ECG reconstruction in the presence of atypical or irregular signal morphologies—corresponding to potentially pathologic cases. Second, in the presence of noise, it does not provide a unique solution for appropriately reconstructing the ECG signals.

The U.S. Pat. No. 7,383,080 and U.S. Patent Publication No. 2008/0065161 describes yet another technique for concatenating the ventricular far field signal (distant signal) observed on the atrium electrode on one hand, with the atrial far field signal (distant signal) observed on the ventricular electrode on the other hand to reconstruct an ECG signal. To connect the two signals at their concatenation, the process includes a step of subtracting a shift to avoid a mismatch, then multiplying each signal by a factor to amplify or attenuate it appropriately.

In the case of a patient with a regular rhythm, this concatenation technique is effective because the two far field signals are well separated. However, for a patient with an irregular rhythm, thus potentially pathological, the far field signals are obscured by the P and R waves and cannot be satisfactorily distinguished from each other. In addition, the proposed processing that simply applies a gain and a time shift reconstructs the ECG signals in a very rough approximation format, and thus does not reproduce the exact morphology of ECG signals.

EP 1 902 750 A1 and its US counterpart US Patent Publication No. 2008 0114259(A1) (ELA Medical) describes a technique for reconstruction of ECG using a principal components analysis (PCA) to extract an endocardial vectogram (VGM) from which a surface vectocardiogram is rebuilt (VCG) to obtain, by a reverse transformation, the reconstructed signals of the different ECG derivations. The reconstruction of the VCG from the VGM is made by a learning phase, including use of a neural network.

These various techniques present certain drawbacks, notably because the EGM and ECG signals, even if they have the same origin, have very different characteristics.

Indeed, electrical activities of a heart reflect the spontaneous stimulations due to the ionic currents in the cardiac cells or artificial stimulations produced by the application of an electrical current to these cells. The EGM (or VGM) signals, directly collected by the implanted device on one or several derivations, reflect the electrical potential of the myocardium, whereas the ECG signals correspond to the electrical potential recorded on the body surface, over a certain number of derivations, after propagating from the myocardium to this body surface.

A satisfactory reconstruction of ECG signals from EGM signals implies taking into account the propagation of the electrical phenomena through the patient's body, and the dependence of transmembrane potential of the ionic currents and of the conductivity of the tissue. These phenomena have been modeled in various forms, generally known as "bidomain models", that are formulated as nonlinear differential equations of the electrical potential, containing linear, quadratic and cubic terms.

But the reconstruction techniques described in the documents cited above rely on a simple linear relationship between EGM and ECG signals, regardless of the physiological knowledge of the bidomain models, with the exception of techniques using neural networks, which introduce non-linear relationships between the EGM and ECG signals. However, the non-linearity introduced by the neural network is simply a sigmoid function or a limiter, and it is very different from the physiological non-linear bidomain model, reflected by the presence of a quadratic term and a cubic term.

Another drawback, specific to all these techniques is that they can not verify that the reconstruction of ECG signal gives a correct result, and even less quantify the quality of this reconstruction.

OBJECT AND SUMMARY OF THE INVENTION

It is, therefore, an object of the present invention to reconstruct ECG signals from the collected EGM signals and to provide a criterion, especially corresponding to an intended use of the reconstructed ECG signals: for a simple determination of the presence or absence of a peak or a QRS complex the ECG signals are reconstructed with an average quality, while for an accurate diagnosis based on specific details of ECG or measurements on it, the ECG signals are reconstructed with a higher quality.

The present invention broadly aims to remedy various drawbacks of prior art techniques by proposing a new technique for reconstruction of ECG signals from EGM signals with a nonlinear filter that is close to physiological non-linearity of a bidomain model. A delay representative of the propagation of electrical signals in body tissues is introduced.

The present invention in a preferred embodiment is based on an approach using non-linear Volterra filters to represent the relationship between EGM signals and ECG signals. The Volterra filters of order 3 introduce quadratic and cubic terms and delays, thereby approach in a much more realistic manner a bidomain model to represent electrical signal propagation in the patient's body between the myocardium and the body surface.

One aspect of the present invention is thus directed to a device for processing signals representative of cardiac potential of depolarization of the myocardium, of the type known according to granted EP 1902750B1 (and its counterpart U.S. Patent Publications 2008/0114257 and 2008/0114259) cited above for processing signals representative of a cardiac potential of depolarization of the myocardium having means for reconstructing an ECG including: a plurality of inputs, receiving a corresponding plurality of EGM signals from endocardial or epicardial electrogram, each EGM signal input being acquired on a respective EGM derivation or channel; at least one output, delivering a reconstructed surface electrocardiogram (ECG) signal related to an ECG derivation; and a digital filter with a non-linear transfer function able to determine said ECG signal based on said plurality of EGM signals.

In a manner characteristic of the present invention, the non-linear digital filter is preferably a Volterra type filter having a transfer function including a linear term and at least one quadratic and/or cubic term.

The technique of Volterra filtering in the medical field is already known, particularly in WO 2008/008692 A2, which describes a Volterra filter applied to the RR signals representative of the cardiac rhythm. But the heart rate is obtained from the ECG or EGM signals by processes that are very different from those of the present invention, without using a reconstruction with non-linear filtering. In fact, the prior art is directed to the characterization of a heart rate variability (HRV), which is a specific problem that is unrelated to that of the present invention. WO 2008/008692 does not use a Volterra filter for generating a reconstructed surface electrocardiogram (ECG) signal from EGM signals directly delivered by an implanted prosthesis.

The Volterra filtering is also a very different technology from that implemented by the EP 1 902 750 A1 cited above because, although the treatment by a neural network for reconstruction of a VCG from a VGM is of a non-linear type, it resembles in no way a Volterra filtering. Indeed, a neural network applies a nonlinear function only to the value of the input x[n] at a given time nT (T being the sampling period), while in a Volterra filter, the linear filtering is applied to quadratic or cubic terms using inputs x[n−k] from earlier instants.

Various forms of advantageous implementations of the present invention include the followings:

The transfer function of the non-linear digital filter preferably comprises at least a finite time delay ($z^{-1}$).

In one embodiment, the device includes a plurality of non-linear Volterra filters (12) each receiving as an input an EGM signal ($x_i[k]$) representing the i-th EGM channel or derivation at time k, and delivering as an output a corresponding filtered signal ($y_{i,j}[k]$), and an adder circuit to combine linearly the filtered signals output by the plurality of non-linear filters, having as the output a reconstructed ECG signal ($y_j[k]$) representing the j-th ECG derivation.

In yet another embodiment, the device includes, for each EGM derivation of a plurality of EGM derivations: a first linear filter receiving as an input the corresponding EGM signals ($x_1[n]$, $x_2[n]$), a second linear filter receiving as an input the same EGM signals squared, and/or a third linear filter receiving as an input the same EGM signals cubed, and means for linearly combining the filtered signals of the first, second and/or third linear filters of each EGM derivation, delivering as an output a reconstructed ECG signal (y[n]). More preferably, the device optionally includes an additional linear filter receiving as an input a cross product of signals of each EGM derivation; and an adder to combine linearly, in addition to the filtered signals by the first, and one or both of the second and third linear filters of each EGM derivation, the signal delivered by said additional filter.

More preferably, two EGM derivations are used, including an atrial EGM derivation and a ventricular EGM derivation.

In yet another embodiment, the device includes means for concatenating sequences of samples ($x_1[n]$, $x_2[n]$ ... $x_Q[n]$) each of them produced at frequency F on each of Q respective EGM derivations, and delivering as an output a concatenated signal (z[n]) of frequency QF; a nonlinear Volterra filter receiving as an input the concatenated signal (z[n]) and delivering as an output a corresponding filtered signal (w[n]) of frequency QF, and means for performing a 1/Q down sampling of said filtered signal (w[n]), and delivering as an output at a frequency F a reconstructed ECG signal (y[n]).

Still another embodiment of the present invention includes means for predetermining the settings of the digital filter, comprising:
  means for collecting EGM signals and at least one acquired ECG signal simultaneously, and
  means for determining parameters of the digital filter, by minimizing a difference between the acquired ECG signal and a reconstructed ECG signal from the acquired EGM signals using the digital filter.

More preferably, the means for determining parameters of the digital filter includes means for directly calculating these parameters using an algorithm for computing a matrix solution satisfying a least squares minimization (LSM) criterion. Alternatively, the means for determining parameters of the digital filter includes means for implementing an algorithm for computing a matrix solution satisfying a composite criterion combining the least squares minimization and a Tikhonov regularization.

In another embodiment, the means for determining parameters of the digital filter include means for iteratively calculating those parameters using a recursive least squares (RLS) algorithm with variable step.

Another aspect of the invention provides the device with means for evaluating the quality of the ECG reconstruction of the non-linear digital filter, comprising:
  means for simultaneously acquiring EGM signals and at least one ECG signal;
  means for determining a reconstructed ECG signal from said acquired EGM signals, and
  means for calculating a correlation coefficient between the acquired ECG signal and the reconstructed ECG signal.

More preferably, the device further includes:
  means for predetermining the settings of the digital filter, and
  means for validating the determining parameters including means for comparing to a given threshold the calculated correlation coefficient and to validate or invalidate those parameters depending on the outcome of said comparison.

It should be understood that the plurality of inputs may correspond to a plurality of EGM signals acquired from electrodes selected from a group of: distal and/or proximal right ventricular electrode, distal and/or proximal right atrial electrode, distal and/or proximal left ventricular electrode, ventricular or atrial defibrillation coil, supra-ventricular defibrillation coil. Further, the device may be an implantable cardiac prosthesis device selected from a group of stimulation, resynchronization, cardioversion and defibrillation type devices. Alternatively, the device may be an external programmer comprising means for downloading and analyzing EGM signals collected by an implanted device, or a home monitor, including means for downloading and analyzing EGM signals collected by an implanted device and producing therefrom data, and means for automatic uploading said data to a remote site. In yet another embodiment, the device may be a data server of a site receiving data from a remote monitor for home monitoring including means for downloading EGM signals collected by an implanted device, and means for automatically transmitting said downloaded EGM signals to said remote site.

Yet another aspect of the present invention is directed to an apparatus for reconstructing a surface electrocardiogram (ECG) from a signal representative of a depolarization potential of a myocardium. One such apparatus includes a plurality of inputs corresponding to a plurality of electrogram (EGM)

signals from an endocardial or epicardial electrogram ($x_1$, $x_2 \ldots x_Q$), each acquired on one EGM derivation respectively; at least one output corresponding to a reconstructed ECG ($y_j$) for an ECG derivation; and a nonlinear digital filter having a transfer function to determine said reconstructed ECG signal for said given ECG derivation in response to said plurality of inputs, said nonlinear digital filter including a Volterra type filter having a transfer function including a linear term ($h_1$) and at least one of a quadratic term ($h_2$) and a cubic term ($h_3$).

The device of the invention thus can be implemented in various forms referenced above.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed, in which like reference characters refer to like elements, and in which.

DETAILED DESCRIPTION OF THE INVENTION

Figure 1:
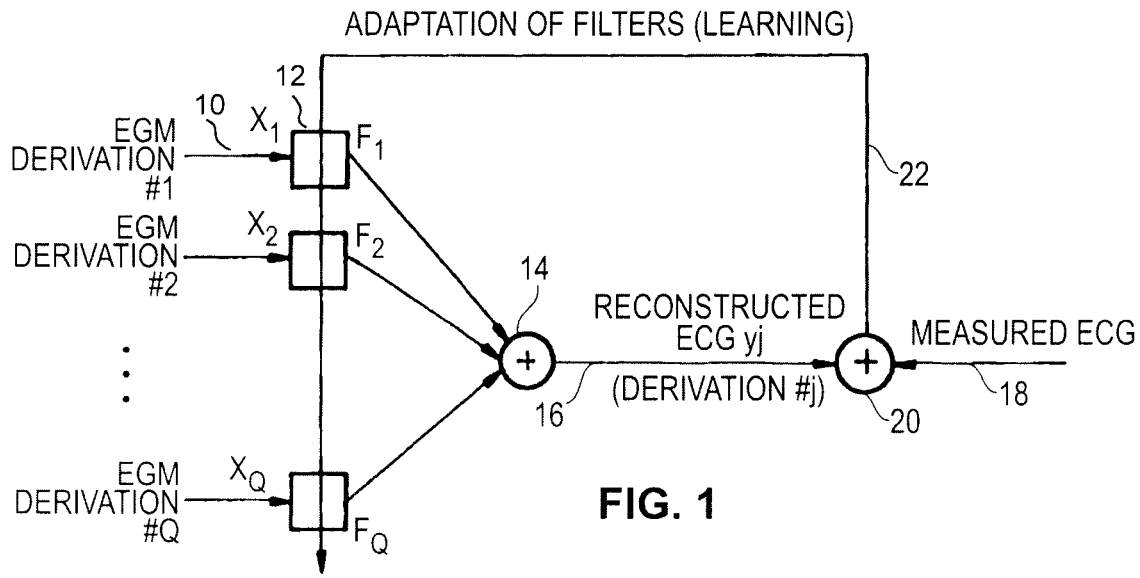
FIG. 1 is a schematic representation of the technique of reconstruction of an ECG, and of learning of the coefficients of the filters in accordance with a preferred embodiment of the present invention.

With reference to the drawings FIGS. 1-5, several examples of implementations of preferred embodiments of the present invention will now be described. Preferably, the functionality and processes of the present invention as described herein can be implemented by an appropriate programming of software of a known implantable pulse generator, for example, a pacemaker or defibrillator/cardioverter, comprising known and conventional circuits and signal acquisition and processing algorithms for acquiring a signal provided through endocardial leads and/or several implanted sensors.

The invention can advantageously be applied to and implemented in the commercial implantable devices marketed by Sorin CRM, Montrouge France, such as the Reply™ and Paradym™ brand pacemakers and comparable commercial and/or proprietary devices of other manufacturers. These devices are equipped with programmable microprocessors, including circuits intended to acquire, condition and process electrical signals collected by implanted electrodes and various sensors, and deliver pacing pulses to implanted electrodes. It is also possible to upload towards these devices, by telemetry, pieces of software (i.e., a software control module) that will be stored in internal memory and run so as to implement the features and functionality of the present invention, as described herein. Implementing the features of the invention into these devices is believed to be easily within the abilities of a person of ordinary skill in the art, and will therefore not be described in detail.

The invention may be implemented within an implant (i.e., direct data processing of the EGM signals by the implanted device), but it may also be implemented in an external programmer used by a practitioner by downloading and analyzing the cardiac signals collected and memorized by an implant.

In yet another advantageous preferred embodiment, the invention is implemented in a home monitor. The home monitor is a special type of programmer whose operation is essentially fully automated without requiring a practitioner. It is particularly intended to allow transmission at regular intervals to a remote site of the collected and analyzed data, e.g. daily, in order to monitor the cardiac condition of the patient remotely.

The invention may also be implemented at a server located at a remote site. For example, the raw EGM data from the implanted device is uploaded to the remote site server directly, without prior processing. The processing is performed by the remote server or a terminal (e.g., a PC computer or programmer) that implements the present invention.

A. Collection of the EGM Signals

The EGM signals are acquired on a plurality of "channels", each channel corresponding to a pair of endocardial or epicardial electrodes connected to the housing of the implanted cardiac device. These channels also are known as "derivations".

The choice of electrodes defining these channels depends on the considered implanted cardiac prosthesis, for example, pacemaker (for treatment of bradycardia), defibrillator (for treatment of tachycardia and fibrillation) or resynchronizer (for treatment of heart failure). Three modes of cardiac stimulation are distinguished: single, dual or triple chamber. These different functions correspond to different choice of electrodes, and to a number of EGM signals different in each situation.

As used herein "RV", "RA" and "LV", respectively, designate the right ventricular, right atrial and left ventricular electrodes of the intracardiac leads with a "+" or "−" sign indicating the distal or proximal position of the electrode, and "CoilV" and "SVC" respectively designate the ventricular and supraventricular defibrillation coils. Thus, the possible combinations of electrodes are (with each time, the possibility to select a bipolar configuration by considering the difference between two electrodes or to select an unipolar configuration by considering the difference between one electrode and the generator housing or CAN):

single chamber: RV+, RV− (and CoilV and in the case of a defibrillator), a single chamber pacemaker provides two EGM signals through the distal and proximal electrodes, the ground being taken on the CAN. The version in a defibrillator delivers three EGM signals through the added CoilV electrode.

dual chamber: RV+, RV−, RA+, RA− (and CoilV and SVC in the case of a defibrillator), a dual-chamber pacemaker provides four EGM signals, and six in a defibrillator version.

triple chamber: RV+, RV−, RA+, RA−, LV+, LV− (and CoilV and SVC in the case of a defibrillator), a triple chamber pacemaker provides six EGM signals, and eight in a defibrillator version.

B. Principle of Reconstruction of the ECG

The ECG signals, which are the manifestation of the cardiac electrical activities on the surface of the patient's body, are well known and normally collected between pairs of electrodes applied in predetermined locations of the patient's chest. Each pair of electrodes determines a "derivation". The whole forms a set of twelve derivations, including bipolar derivations (I, II, III), unipolar derivations (aVF, aVR, aVL) and precordial derivations (V1 to V6).

According to one embodiment, the present invention reconstructs one or more of these ECG signals from the signals collected in the form of a plurality of EGM derivations. The basic principle of this reconstruction is schematically shown in FIG. 1. A plurality of EGM signals $x_1, x_2 \ldots x_Q$, are collected and sampled on Q EGM channels (10). Each of these signals is applied to a respective filter $F_1, F_2 \ldots F_Q$, (reference 12). The output signals of each of these filters 12 are linearly combined in adder 14 to produce a reconstructed ECG signal 16, corresponding to one of the twelve derivations to be reconstructed. The reconstructed signal 16 on the derivation No. j will be designated $y_j$. Other ECG derivations are reconstructed by the same technique but typically with different filter settings.

The setting of the filters corresponding to an ECG derivation is achieved by a learning process that includes comparing the reconstructed ECG signal 16 to an ECG signal 18 actually measured on the considered derivation. These two signals are applied to a linear differentiator 20 delivering an error signal 22 to ensure, through learning, an adaptation and setting of filters 12. This stage of learning, which will be explained in more detail in the following description, is essentially to calculate, for each of the filters $F_1, F_2 \ldots F_Q$, the parameters (i.e., coefficients) of these filters that minimize the difference between the reconstructed ECG and the ECG actually measured.

C. Principle of Volterra Filtering

In a preferred embodiment of the invention, filters $F_1, F_2 \ldots F_Q$ are Volterra type non-linear filters. The Volterra filter is described, for example by Schetzen M, "The Volterra and Wiener Theories of Nonlinear Systems," Wiley and Sons, New York, 1980, or by V J Mathews, "Adaptive Polynomial Filters", IEEE Signal Processing Magazine, 8 (3) pp. 10-26, July 1991. Volterra filters allow in particular establishing a non-linear relationship between the EGM signals and the ECG signals similar to the one of a bidomain model that includes linear, quadratic and cubic terms. They also introduce in this relationship a finite delay reflecting the propagation of the electrical signals through body tissues from the myocardium to the surface of the patient's skin.

Specifically, a Volterra filter receives as input discrete real time signal x[n], with n being an integer (n being the rank of the sample signal), and generates an output y[n] defined by:

$$y[n] = h_0 + \sum_{m=1}^{p} \sum_{k_1=0}^{N_1-1} \ldots \sum_{k_p=0}^{N_m-1} h_m[k_1, \ldots, k_m]x[n-k_1] \ldots x[n-k_m]$$

This equation defines an input-output relationship of a Volterra filter of the p-th order.

In the following description, the order of the Volterra filter is limited to p=3, but it should be understood that this simplification is in no manner a limitation and the invention also contemplates the use of higher order filters. In the embodiment of order p=3, the above equation becomes:

$$y[n] = h_0 + \sum_{k=0}^{N-1} h_1[k]x[n-k] + \sum_{k=0}^{P-1}\sum_{l=0}^{P-1} h_2[k,l]x[n-k]x[n-l] +$$

$$\sum_{k=0}^{M-1}\sum_{l=0}^{M-1}\sum_{r=0}^{M-1} h_3[k,l,r]x[n-k]x[n-l]x[n-r]$$

This equation can be simplified as:

$$y[n]=h_0+h_1(N)+h_2(P)+h_3(M)$$

where $h_0$ is a constant term, independent of the input, $h_1$ is a linear filter, $h_2$ a quadratic filter and $h_3$ a cubic filter (the term $h_m$ is called "kernel of order m" filter). It should be understood that such a filter is causal, since it only involves the previous values at time n. Here, N represents the "memory" of the linear filter $h_1$, corresponding to more or less the important part of the past of the inputs involved in the construction of the present output, P and M representing, in the same way, the memory of quadratic $h_2$ and cubic $h_3$ filters. In the published literature, Volterra filters generally have identical memories N, M and P, but in the case of the present invention, it is preferable to use different memory for each kernel $h_m$ in order to reduce certain kernels memory and hence reducing the overall complexity of computing.

Figure 2:
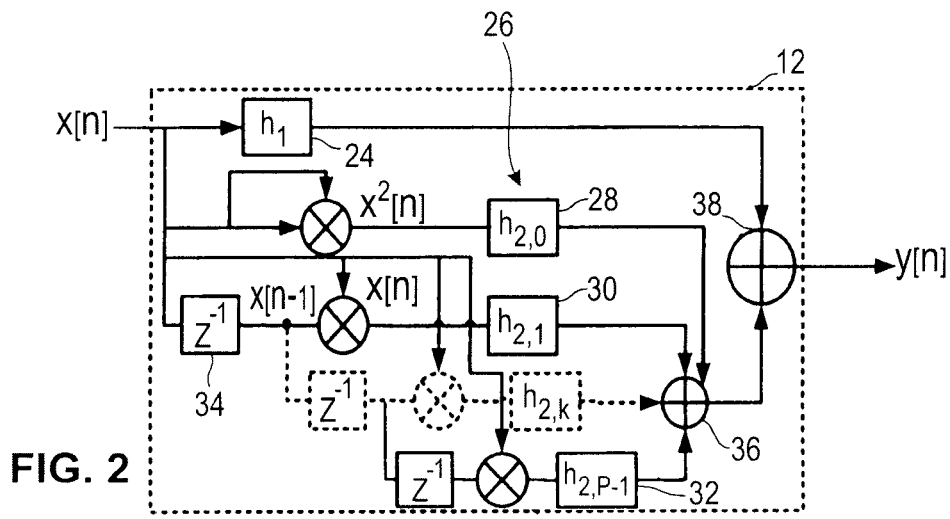
FIG. 2 is a block diagram illustrating an implementation of a Volterra filter of order 2 for a system with one input and one output.

With reference to FIG. 2, details are illustrated of an embodiment implementing a Volterra filter of second order. For simplicity, the present example does not have a constant term. This filter 12 comprises an input x[n] and an output y[n].

The linear kernel 24 (term $h_1$) acts directly on the input signal. The quadratic kernel 26 (term $h_2$) has P linear filters 28, 30, 32, and so on. The first linear filter 28, $h_{2,0}$ of the quadratic kernel 26 acts on the signal x[n] multiplied by itself, that is $x[n]x[n]=x^2[n]$. The second linear filter 30, $h_{2,1}$ of the quadratic kernel 26 acts on the signal x[n] multiplied by that same signal delayed by one sample. The operator $z^{-1}$ of the block 34 represents a delay of one sample. The input of the second linear filter 30 is the signal x[n]x[n−1]. This process repeats and the last linear filter $h_{2,P-1}$ of the quadratic kernel 26 acts on the signal x[n]x[n−P−1].

In its general form, the quadratic filter $h_2$ is a P×P matrix of two-dimensional elements, and the filter cube $h_3$ is a three-dimensional matrix of M×M×M elements. If one eliminates from these matrices the redundant terms, the number of coefficients is reduced, and the general equation of a Volterra filter of third order becomes:

$$y[n] = h_0 + \sum_{k=0}^{N-1} h_1[k]x[n-k] + \sum_{k\geq l}^{P-1}\sum_{l=0}^{P-1} h_2[k,l]x[n-k]x[n-l] +$$

$$\sum_{k\geq l}^{M-1}\sum_{l\geq r}^{M-1}\sum_{r=0}^{M-1} h_3[k,l,r]x[n-k]x[n-l]x[n-r]$$

Note that if $h_0=0$ and if P=0 and M=0 (i.e., no memory of the past for quadratic and cubic kernels), this equation is reduced to a conventional convolution of a transverse linear filter, also known as a finite impulse response (FIR) filter.

D. First Mode of Implementation of the Invention

In the case of a reconstruction of ECG signals from EGM, the system receives multiple inputs depending on the number measurable by the implant EGM channels and outputs one or more ECG derivations (e.g., from one to twelve depending on the number of desired). Such a system is of multi-input/multi-output (MIMO) type.

To simplify the discussion below, each ECG derivation will be considered separately, and the reconstruction of one ECG derivation from a plurality of input EGM channels (a multi-input/single output (MISO) system) is described below. The reconstruction method can obviously be generalized to a plurality of ECG derivations, each with its own filter coefficients.

Figure 3:
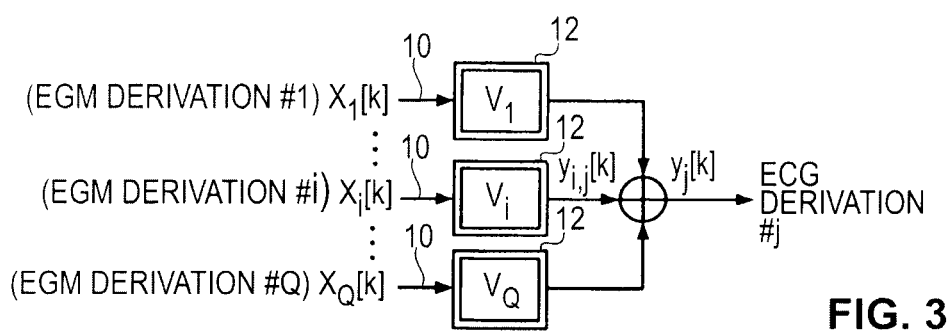
FIG. 3 is a block diagram of a first embodiment of the present invention, allowing the reconstruction of an ECG derivation from three EGM channels.

This first implementation is made with reference to FIG. 3. A Volterra filter (filter 12) is applied to each EGM derivation 10. The outputs of filters 12 are subjected to a linear combination using adder 14 to reconstruct the ECG derivation from all the filtered channels.

If we designate $x_i[k]$ the discrete signal of the EGM channel No. i, and $h_m^{i,j}$ the Volterra filter kernel of order m driven by this signal $x_i[k]$ to reconstruct the signal $y_j[k]$ representing the ECG derivation (reconstructed) n° j, the output $y_{i,j}[k]$ of the Volterra filter 12 is given by:

$$y_{i,j}[n] = h_0^{i,j} + \sum_{k=0}^{N-1} h_1^{i,j}[k]x_i[n-k] + \sum_{k\geq l}^{P-1}\sum_{l=0}^{P-1} h_2^{i,j}[k,l]x_i[n-k]x_i[n-l] + \sum_{k\geq l}^{M-1}\sum_{l\geq r}^{M-1}\sum_{r=0}^{M-1} h_3^{i,j}[k,l,r]x_i[n-k]x_i[n-l]x_i[n-r]$$

The signal $y_j[k]$ of the ECG derivation n° j reconstructed from the Q signals $y_{i,j}[k]$ is given by:

$$y_j[n] = \sum_{i=1}^{Q} y_{i,j}[n]$$

It is demonstrated that the number of unknowns to be determined to reconstruct a (unique) ECG derivation from Q EGM channels is equal to:

$$K_1 = 1 + Q[N+P(P+1)/2+M(M+1)(M+2)/6]$$

It is possible to cancel some kernels $h_m$ to reduce the number of unknowns in the system to solve, for example, by using only quadratic Volterra filters of order 2, with M=0. Alternately, one may choose to cancel the quadratic term (P=0) and keep the cubic term.

E. Second Mode of Implementation of the Invention

The second embodiment of the present invention uses a simplified version of the Volterra filter to take into account the products $x_i[n-k]x_i[n-l]$ between the temporal samples of the same input signal $x_i[k]$ taken at the same sampling moments. This is equivalent to apply linear filters to their squares $x_i[k]$ $x_i[k]=x_i^2[k]$ . . . (diagonal terms of the kernels $h_m$).

The contribution of the signal $x_i[k]$ of the EGM derivation n° i in the construction of the ECG derivation y[k] is then:

$$y_i'[n] = h_0^i + \sum_{k=0}^{N-1} h_1^i[k]x_i[n-k] + \sum_{k=0}^{P-1} h_2^i[k]x_i^2[n-k] + \sum_{k=0}^{M-1} h_3^i[k]x_i^3[n-k]$$

With this simplified version, it may be advantageous to also take into account the cross-products $x_c[k]$ between several EGM inputs on the same sampling moments. In this case, the equation of the reconstructed ECG signal is:

$$x_c[k] = x_1[k]x_2[k] \ldots x_Q[k]$$

$$y[n] = \sum_{i=1}^{Q} y_i'[n] + \sum_{s=0}^{N-1} h_c[s]x_c[n-k]$$

The number of unknown variables is: 1 for the constant term, QN for the linear term, QP for the quadratic term, QM for the cubic term and N for the cross product term, or $K_2=1+N+Q(N+P+M)$ unknowns to be determined.

Figure 4:
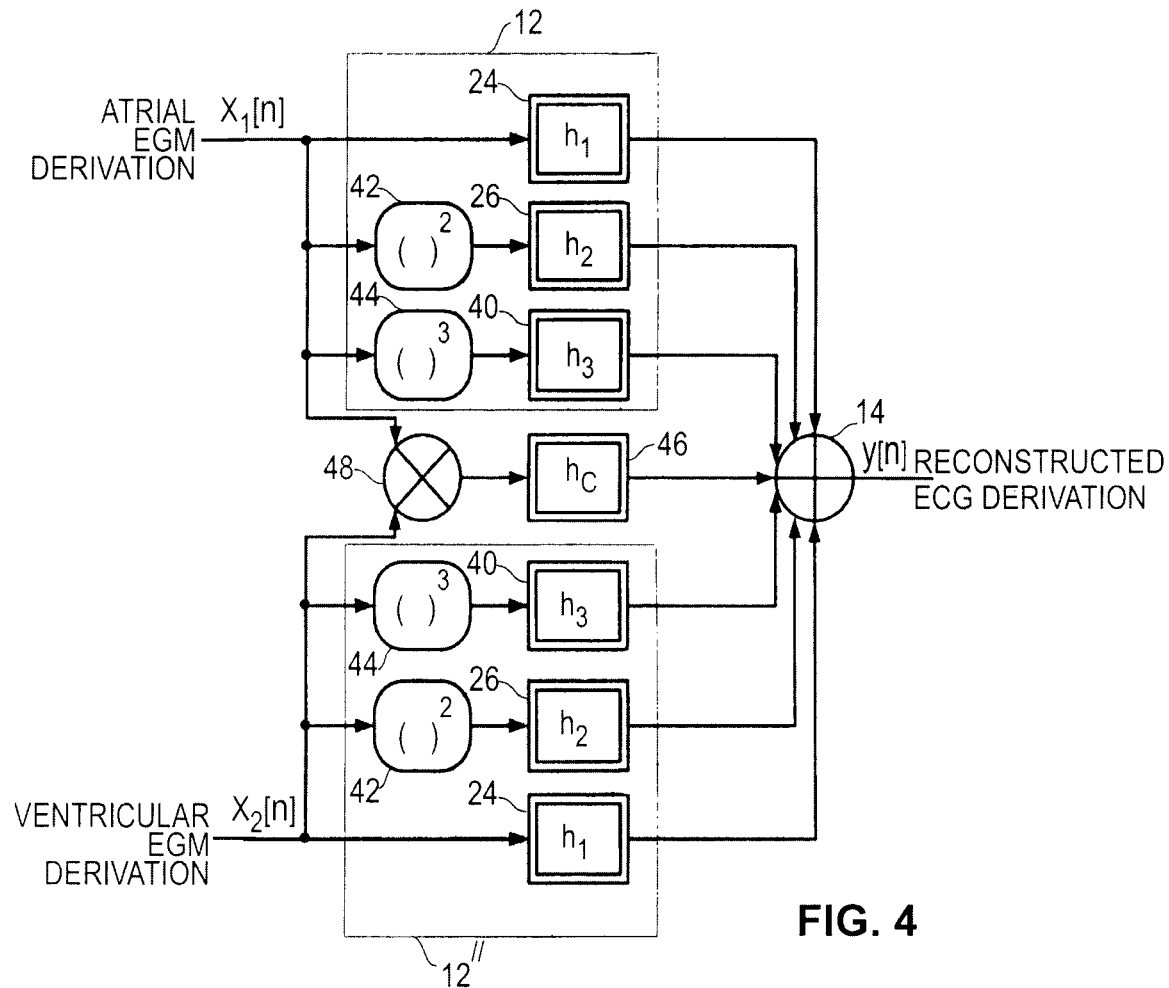
FIG. 4 is a block diagram of a second embodiment of the present invention, allowing the reconstruction of an ECG derivation from an atrial and a ventricular EGM channel.

With reference to FIG. 4, the block diagram illustrates the second implementation with two input EGM channels, namely:

the signal $x_1[n]$ representing the EGM collected by a lead located in an atrium, and the signal $x_2[n]$ representing the EGM collected by a lead located in a ventricle.

The block 12' represents a first simplified Volterra filter, acting on the diagonal terms only. It contains three linear filters 24, 26, 40 representing the three kernels of that filter, which respectively receive the signal $x_1[n]$, its square 42, and its cube 44. Block 12" performs the same operations respectively on the signal $x_2[n]$.

The filter 46 is a linear filter that receives as an input the cross product 48 of $x_1[n]$ and $x_2[n]$ signals; $x_1[n]$ is the signal collected in the atrium and $x_2[n]$ is the signal collected in the ventricle; the cross product $x_c[k]=x_1[k]x_2[k]$ is a signal close to the far-field signal because the signal $x_2[n]$ is attenuated everywhere except at the moments when the P wave occurs; and the signal $x_1[n]$ is reduced everywhere except at the moments when the R wave occurs. In other words, the signal $x_c[k]$ represents the signal acquired by the atrial lead, amplified at the moments when the R wave occurs.

The ECG signal is calculated by an adder 14 making a linear combination of outputs of Volterra filter 12' and 12" and of the output $h_c$ of filter 46 (the constant term $h_0$ is omitted in this figure). This simplified version has the advantage of a reduced complexity as compared to the full version of the first implementation, taking into account non-linearity of a bidomain model.

As in the case of the first implementation, it is possible to further reduce the complexity of the Volterra filter of the second implementation by cancelling some kernels of order 2 or 3 in particular.

F. Third Mode of Implementation of the Invention

Figure 5:
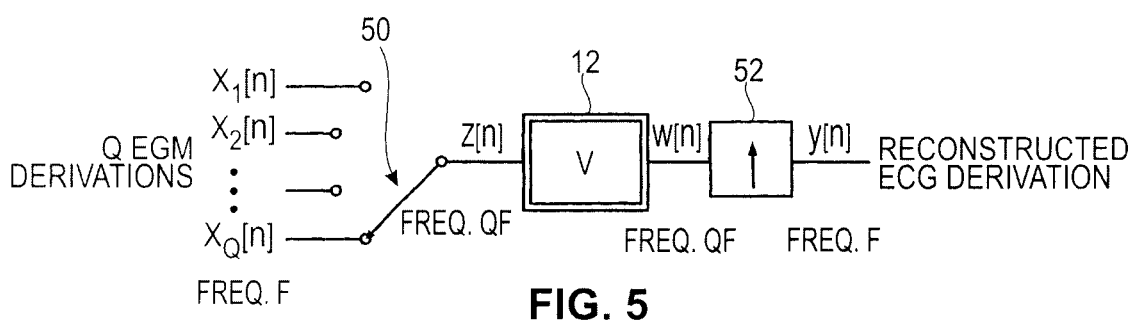
FIG. 5 is a block diagram of a third embodiment of the present invention, allowing the reconstruction of an ECG derivation using a single Volterra filter.

The third embodiment implementing the present invention uses only one Volterra filter for the reconstruction of an ECG derivation, irrespective of the number Q of EGM channels. The technique, illustrated with reference to FIG. 5, is to produce a signal z[n] consisting of a concatenation of successive EGM signals $x_i[n]=x_1[n], x_2[n] \ldots x_Q[n]$. For each sampling instant nT, the signal z is built using all the Q values of signals $x_i[n]$. Thus, if the sampling frequency of the EGM signals is F, the frequency of the signal z[n] is equal to QF.

According to one embodiment, the function 50 is implemented by a parallel to series converter, or by a circular switch 50 switching between the Q input signals at a frequency QF.

Volterra filter 12 is applied to the signal z[n] thus formed, and produces an output signal w[n], also at the frequency QF.

The signal y[n] at frequency F, is extracted from the signal w[n] by down-sampling of order Q by keeping a value every Q values (block 52).

This implementation involves cross products between the values of various input signals, taken at different sampling instants. Since Volterra filter 12 works at frequency QF it requires Q times more memory, to cover the same past of the signal, than the same filter operating at frequency F.

The number of unknowns to be determined to reconstruct an ECG derivation from Q EGM channels is:

$$K_3=1+[QN+QP(QP+1)/2+QM(QM+1)(QM+2)/6]$$

The complexity of Volterra filter 12 is mainly based on the number of channels Q of EGM derivations in input.

G. Determination of Coefficients of Volterra Filters

As stated above, the determination of the coefficients of the Volterra filters used to reconstruct the ECG is based on a learning process operated in a first step by collecting simultaneously a set of reference data consisting of EGM signals $x_i^R[k]$ and of ECG signals $y^R[k]$ synchronized with the EGM signals.

The number of unknowns to be determined in the system depends on the size of N, P and M memories of the filters, and the length of the training sequence should be sufficient for an unambiguous determination of the filter coefficients (greater than the number of unknowns in the Volterra system).

The filtering equations developed above are expressed in a simpler form. The basic idea is that the output is generally linear in terms of the parameters h, although it is not linear in input x. This allows to write the input-output relationship as a scalar product of properly defined vectors.

In the case of the first embodiment of implementation of the invention, a vector of unknowns H, of size $K_1$ defined above, is formed by the concatenation of several sub-vectors $h_m^i$, each representing the coefficients of the kernel of order m driven by the EGM derivation signal No. i:

$$H=[h_0,h_1^1,h_2^1,h_3^1,\ldots,h_1^Q,h_2^Q,h_3^Q]^T$$

This simplification of the kernels is reused for the input signal. In particular, the vector $x_i[n]=\{x_i[n],\ldots,x_i[n-N-1]\}$ of the EGM input No. i is associated to the vector $x_m^i$ representing the non-redundant terms implied in the kernel of order m:

$$x_1^i[n]=x_i[n]$$

$$x_2^i[n]=\{x_i[n-k]x_i[n-l]\}_{P>k\geq l\geq 0}$$

$$x_3^i[n]=\{x_i[n-k]x_i[n-l]x_i[n-r]\}_{M>r\geq k\geq l\geq 0}$$

A global vector X representing the total contribution of all Q EGM inputs:

$$X[n]=[1,x_1^1[n],x_2^1[n],x_3^1[n],\ldots,x_1^Q[n],x_2^Q[n],x_3^Q[n]]^T$$

The constant 1 represents the input signal to the constant term $h_0$ of the filter.

The input-output relationship described above for the first embodiment of implementation takes a simplified form:

$$y[n]=X[n]^T H$$

In the case of second and third modes of implementation, the equations are transformed into a scalar product of two vectors, namely a vector H containing the filter coefficients and a vector X containing quantities calculated from products formed between the input values for different sampling instants.

H. Determination of Filter Coefficients (First Technique—Regularization Tikhonov)

With a reference set containing EGM signals and ECG signals acquired simultaneously, the above equation allows to deduce the filter H that best fits this equation. Several techniques may be implemented to achieve this result.

A first matrix technique is to transform the previous vector equation to a matrix equation, using all data. Assuming that the dataset has already been acquired before, the conversion can be done offline (batch mode). Let L be the size of data set reference, and $n_0=\max(N,P,M)$ the maximum memory of the kernels of the Volterra filter. We now have $L-n_0$ vector equations that are grouped as:

$$\begin{bmatrix} y^R[n_0] \\ \vdots \\ y^R[n] \\ \vdots \\ y^R[L-n_0] \end{bmatrix} = \begin{bmatrix} X_R[n_0]^T \\ \vdots \\ X_R[n]^T \\ \vdots \\ X_R[L-n_0]^T \end{bmatrix} H$$

Or $$Y=\overline{A}H$$

Y being a vector of $L-n_0$ values of a given ECG derivation, $\overline{A}$ being a matrix of $(L-n_0)\times K_1$ non-redundant elements formed from the EGM inputs, and H being a vector of $K_1$ unknowns representing the Volterra filter coefficients.

The fact that the matrix $\overline{A}$ is composed of elements that are not formally redundant does not guarantee that it is numerically well conditioned to ensure a unique and stable solution H obtained in solving the linear (in H) system above. Note also that the values of ECG in Y and the EGM values used in $\overline{A}$ are affected by various types of noise. This makes the linear system an "ill-posed inverse problem" in the sense that the matrix $\overline{A}$ is a "ill-conditioned matrix". i The least squares solution of the linear system that minimizes the norm of the difference between the values Y of the acquired ECG and the ECG values calculated by the solution $H_{LS}$ is given by:

$$H_{LS}=(\overline{A}^T\overline{A})^{-1}\overline{A}^T Y$$

This solution $H_{LS}$ minimizes the least squares criteria $\|Y-\overline{A}H\|^2$.

To ensure a numerically stable solution, the present invention proposes to use a regularization that finds a solution satisfying a composite criterion, by adding a constraint to the constraint of the least squares. This regularization, known as a "Tikhonov regularization", is described as a general principle, especially by A N Tikhonov and V A Arsenin, "Solution of Ill-Posed Problems," Winston & Sons, Washington, 1977 (ISBN 0-470-99124-0). The composite criterion used is written:

$$\|Y-\overline{A}H\|^2+\lambda\|\Gamma H\|^2$$

Where $\Gamma$ is the Tikhonov matrix. Often this matrix is chosen as the identity matrix $\Gamma=I$, to favour solutions with a low norm and hence to ensure numerical stability. In other cases, the matrix $\Gamma$ may present an operator of first order difference to obtain smooth solutions. The parameter $\lambda$ is called the regularization parameter and represents a tradeoff between the least squares criterion and the additional Tihkonov criterion. The regularized solution is given by:

$$H_{Tikh}=(\overline{A}^T\overline{A}+\lambda\Gamma^T\Gamma)^{-1}\overline{A}^T Y$$

Several techniques for choosing the regularization parameter $\lambda$ can be found in the literature, the method of "cross validation" being the most common.

This first technique for determining the coefficients of the Volterra filter provides a high quality of reconstruction. However, it may not be practical in a real time application because it requires the combination of the reference EGM data in a matrix. It also requires a relatively large memory because the size of the formed matrix depends on the size of the reference data. It is therefore preferably implemented in a programmer communicating with the implant and having a fast processor and large memory size.

I. Determination of Filter Coefficients (Second Technique—Recursive Least Squares)

Another technique that is used to determine the coefficients of the filter is the Recursive Least Squares (RLS). An example of this method is described by Hayes, MH (1996), "Recursive Least Squares, Statistical Digital Signal Processing and Modeling," Wiley, p. 541 (ISBN 0-471-59431-8), or by S Haykin, Adaptive Filter Theory, Prentice Hall, 2002 (ISBN 0-13-048434-2).

This approach solves linear system $y[n]=X[n]^T H$ in real-time (on-line), and requires less computational resources for calculating the coefficients. It is therefore implemented in an implanted device without the need for an external programmer. This iterative method uses a variable step to control the convergence speed during iterations, which represents an advantage in multi-input systems compared to iterative methods with fixed step like LMS. The RLS forgetting factor plays the role of the regularization of the matrix method of Tikhonov.

J. Assessing the Quality of the Reconstruction of the ECG

Another aspect of the present invention concerns assessing the quality of the reconstruction of the ECG. The quality of the reconstruction is estimated, for example, to choose a particular reconstruction technique based on an acceptable tradeoff between hardware limitations (computation time, hardware and software resources available) and the actual needs according to the intended use of the reconstructed ECG (e.g., detecting the mere presence of certain characteristics, or further examination of waveforms).

To assess the quality of the reconstruction, the EGM and ECG signals (ECG signals that are actually collected) are acquired simultaneously during a measurement period $T_m$. This period $T_m$ must be at least two cardiac cycles long (approximately 2 s) and may be extended up to 100 or 1000 seconds. The sequences chosen as a set of reference data for the learning process has duration $T_r$ of at least one second and can be extended up to 99 or 999 seconds. The EGM and ECG signals are acquired simultaneously during a period $T_m$, for example, with a sampling rate of 128 Hz.

If the sampling frequency of the ECG and EGM (usually located in the range 100 Hz to 1 kHz) are different, it is necessary to synchronize the data by a suitable technique, such as interpolation (linear, polynomial or splines) or compression (e.g., turning point Mueller algorithm).

The quality of the reconstruction of the ECG signals is evaluated by a numerical criterion that involves determining, for a sequence that has not been used for the learning process, the correlation coefficient $\rho$ between the real ECG signals $y[k]$ and the reconstructed ECG signals $y_{rec}[k]$.

Specifically, a shift or a time delay in the order of 40 ms (i.e., a shift of d=5 samples for a sampling frequency of 128 Hz) in the reconstructed signal does not alter the capacity to diagnose the ECG signals.

The correlation coefficient is evaluated for each shift k:

$$\rho_k = \frac{\sum_{i=0}^{J}(y[i]-\bar{y})(y_{rec}[i+k]-\bar{y}_{rec})}{\sqrt{\sum_{i=0}^{J}(y[i]-\bar{y})^2}\sqrt{\sum_{i=0}^{J}(y_{rec}[i+k]-\bar{y}_{rec})^2}}$$

The quality of reconstruction (between −1 and +1) is estimated by:

$$\rho = \max_{-d \leq k \leq d}(\rho_k)$$

For ECG sequences that have a regular rhythm, the present invention provides a quality reconstruction superior to 97% from bipolar signals from the atrium and from the ventricle (the proximal signal being considered by reference to the distal signal). The reconstructed ECG signals faithfully reproduce the polarity, width and position of the QRS complex in the ECG.

The quality of reconstruction obtained by the present invention is very high in comparison to that obtained with methods based on known neural networks, which is only about 85% when using two bipolar, atrial and ventricular, signal for a patient having a regular cardiac rhythm. Specifically, the quality of reconstruction should be of the order of at least 60 to 65% in order to find in the reconstructed ECG certain peculiarities that we look to determine its presence or absence like (peaks, polarity, etc . . . ). These peculiarities may be sufficient for a quick patient follow-up visit for ECG monitoring. However, in order to establish a more accurate diagnosis from a detailed examination of waveforms, the quality of reconstruction should be at least about 80%.

The quantified quality of reconstruction is especially used to validate the calculation of the filter coefficients in the learning process. Thus, after calculating the filter parameters, the quality of reconstruction is compared to a threshold value. This threshold is programmable and is adjusted if necessary by the practitioner, or is preset to an acceptable value, e.g. 65%.

If the quality criterion is verified (threshold is exceeded), the estimated coefficients are stored, and the calculated filter is used for later reconstruction of the considered ECG derivation. The process is optionally repeated for each ECG derivation to be used. However, if the criterion is not verified, it is necessary to restart the determination of the filter parameters, either by selecting a different reference period $T_r$ in the measurement window $T_m$ (in the window $T_r$, there were perhaps arrhythmias that might interfere with the learning process), or by repeating the acquisition of another data set over another length Tm.

One skilled in the art will appreciate that the present invention can be protected by embodiments other than those described herein, which are provided for purposes of illustration and not of limitation.

The invention claimed is:

1. A method for reconstructing a surface electrocardiogram (ECG), the method comprising:
    receiving, a plurality of inputs, corresponding to a plurality of signals from endocardial or epicardial electrograms, each of the plurality of signals acquired on a respective channel of a plurality of channels;
    filtering each of the plurality of inputs with a corresponding non-linear, digital Volterra type filter, each of the corresponding non-linear, digital Volterra type filters having a transfer function including a linear term and at least one quadratic and/or cubic term(s); and
    combining each of the filtered plurality of inputs to reconstruct at least one reconstructed surface electrocardiogram ECG signal.

2. The method of claim 1, wherein the transfer function of each of the non-linear digital filters further comprise at least a finite time delay.

3. The method of claim 1, wherein combining further comprises
linearly combining the signals filtered by each of corresponding non-linear digital Volterra filters.

4. The method of claim 1, comprising:
receiving, at a first linear filter, as an input one of the plurality of inputs;
receiving, at a second linear filter, as an input the one of the plurality of inputs squared;
receiving, at a third linear filter, as an input the one of the plurality of inputs cubed; and
linearly combining the filtered signals of the first, second and/or third linear filters to reconstruct the ECG signal.

5. The method of claim 4, further comprising:
filtering, with an additional linear filter, a cross product of each of the plurality of inputs; and
linearly combining the filtered cross product of each of the plurality of inputs with the filtered signals from the first and one or both of the second and third linear filters.

6. The method of claim 5, wherein a first of the plurality of inputs includes an atrial EGM derivation and a second of the plurality of inputs includes a ventricular EGM derivation.

7. The method of claim 1, comprising:
concatenating sequences of samples produced at a frequency from each of the plurality of received inputs;
filtering, with a nonlinear Volterra filter, said concatenated signal.

8. The method of claim 1, further comprising predetermining the settings of each of the corresponding non-linear, digital Volterra type filters by:
receiving the plurality of inputs and at least one acquired ECG signal simultaneously, and
determining parameters of the corresponding non-linear digital Volterra type filters by minimizing a difference between said acquired ECG signal and the reconstructed ECG signal.

9. The method of claim 8, wherein determining the parameters of the digital filter further comprises directly calculating said parameters using an algorithm for computing giving a matrix solution satisfying a least squares minimization criterion.

10. The method of claim 9, wherein determining the parameters of the digital filter further comprises implementing an algorithm for computing a matrix solution satisfying a composite criterion combining the least squares minimization and a Tikhonov regularization type of constraint.

11. The method of claim 8, wherein the determining the parameters of the digital filter further comprises iteratively calculating those parameters using a recursive least squares (RLS) algorithm with a variable step.

12. The method of claim 1, further comprising evaluating the quality of the reconstructed surface ECG signal by:
simultaneously acquiring the plurality of inputs and at least one ECG signal;
determining the reconstructed ECG signal; and
calculating a correlation coefficient between the acquired ECG signal and the reconstructed ECG signal.

13. The method of claim 12, further comprising:
predetermining settings of the digital filter, and
validating the predetermined settings by comparing to a given threshold the calculated correlation coefficient to validate or invalidate the predetermined parameters depending on the outcome of said comparison.

14. The method of claim 1, wherein said plurality of inputs correspond to the plurality of EGM signals acquired from electrodes selected from a group consisting of: distal and/or proximal right ventricular electrode, distal and/or proximal right atrial electrode, distal and/or proximal left ventricular electrode, ventricular or atrial defibrillation coil, supra-ventricular defibrillation coil.

15. The method of claim 1, further comprising downloading and analyzing the received inputs.

16. The method of claim 1, further comprising:
downloading and analyzing the received inputs;
producing therefrom data; and
automatically uploading said data to a remote site.

* * * * *